(12) United States Patent
McCrory

(10) Patent No.: US 10,342,712 B1
(45) Date of Patent: Jul. 9, 2019

(54) DISPOSABLE FEMININE-HYGIENE PRODUCT

(71) Applicant: Samantha A. McCrory, Grapevine, TX (US)

(72) Inventor: Samantha A. McCrory, Grapevine, TX (US)

( * ) Notice: Subject to any disclaimer, the term of this patent is extended or adjusted under 35 U.S.C. 154(b) by 823 days.

(21) Appl. No.: 14/810,686

(22) Filed: Jul. 28, 2015

Related U.S. Application Data

(60) Provisional application No. 62/031,552, filed on Jul. 31, 2014.

(51) Int. Cl.
*A61F 13/26* (2006.01)
*A61F 13/20* (2006.01)

(52) U.S. Cl.
CPC .......... *A61F 13/26* (2013.01); *A61F 13/2051* (2013.01)

(58) Field of Classification Search
CPC ........ A61F 13/263; A61F 13/266; A61F 6/20; A61F 13/26; A61F 13/2051; A61F 15/002; A61F 15/003; A61F 6/12; A61M 31/00; A61M 2205/27; A61M 5/3271; B43K 24/14; B43K 8/24
USPC .............................................. 604/11–18, 385
See application file for complete search history.

(56) References Cited

U.S. PATENT DOCUMENTS

| | | | | |
|---|---|---|---|---|
| 3,807,399 | A * | 4/1974 | Morman | A61F 13/26 604/14 |
| 2014/0058428 | A1 * | 2/2014 | Christopher | A61B 5/15117 606/182 |
| 2015/0164702 | A1 * | 6/2015 | Mueller | A61F 13/2034 604/369 |

FOREIGN PATENT DOCUMENTS

WO WO 2005107671 A1 * 11/2005 ......... A61F 13/2051

\* cited by examiner

*Primary Examiner* — Jan Christopher L Merene
*Assistant Examiner* — Cana A Gallegos
(74) *Attorney, Agent, or Firm* — Kenneth L Tolar

(57) ABSTRACT

A disposable, feminine-hygiene product includes an elongated, hollow tube formed of a lower section telescopically received within an upper section. The top end of the upper section includes a plurality of frangible leaves that immediately separate upon impact. Received within the tube interior is a telescoping shaft having a lower end attached to a knob that, when rotated, releases a spring-biased cylinder to thrust a plurality of absorbent strips through the frangible leaves.

6 Claims, 2 Drawing Sheets

DISPOSABLE FEMININE-HYGIENE PRODUCT

CROSS REFERENCE TO RELATED APPLICATIONS

This application is entitled to the benefit of provisional patent application No. 62/031,552 filed on Jul. 31, 2014, the specification of which is incorporated herein by reference.

BACKGROUND OF THE INVENTION

The present invention relates to a feminine-hygiene product that automatically deploys a bundle of fabric strands to absorb unwanted fluids.

DESCRIPTION OF THE PRIOR ART

Most women douche in order to remove unwanted bodily fluids caused by an infection or a menstrual cycle. However, the practice is discouraged by most gynecologists since it also removes beneficial microorganisms from the vaginal area. Furthermore, because a douche effluent does not immediately drain, the entire task can be time consuming. Accordingly, there is currently a need for hygienic product that efficiently removes unwanted fluids. The present invention addresses this need by providing a disposable insert that automatically deploys a bundle of compacted fabric strips to absorb unwanted fluids.

SUMMARY OF THE INVENTION

The present invention relates to a disposable, feminine-hygiene product comprising an elongated, hollow tube formed of a lower section telescopically received within an upper section. The top end of the upper section includes a plurality of frangible leaves that immediately separate upon impact. Received within the tube interior is a telescoping shaft having a lower end attached to a knob that, when rotated, releases a spring-biased cylinder to thrust a plurality of absorbent strips through the frangible leaves.

It is therefore an object of the present invention to provide a feminine-hygiene product that allows a user to easily remove unwanted vaginal fluids.

It is another object of the present invention to provide a feminine hygiene product that automatically deploys a bundle of fibers to remove unwanted fluids.

Other objects, features, and advantages of the present invention will become readily apparent from the following detailed description of the preferred embodiment when considered with the attached drawings and the appended claims.

DESCRIPTION OF THE PREFERRED EMBODIMENT

Figure 1:
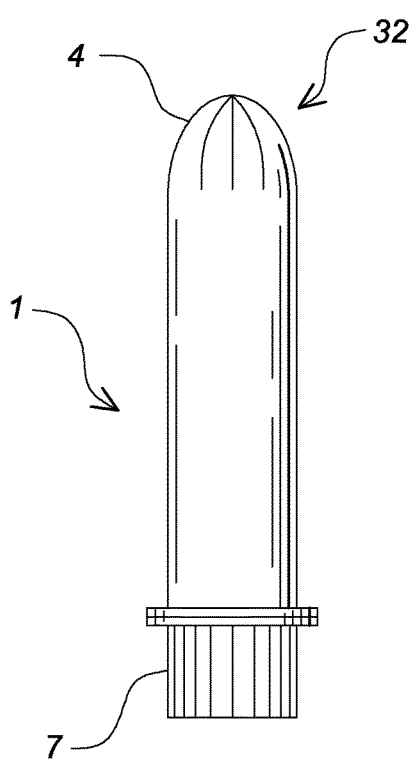
FIG. 1 is a plan view of the feminine-hygiene product according to the present invention with the tube in a collapsed position.
Figure 2:
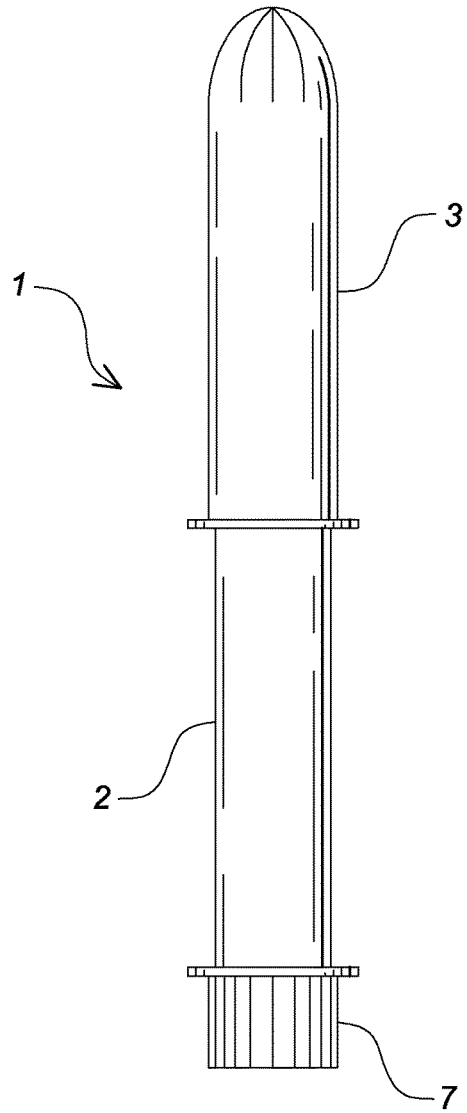
FIG. 2 is a plan view of the feminine-hygiene product with the tube in an expanded position.
Figure 3:
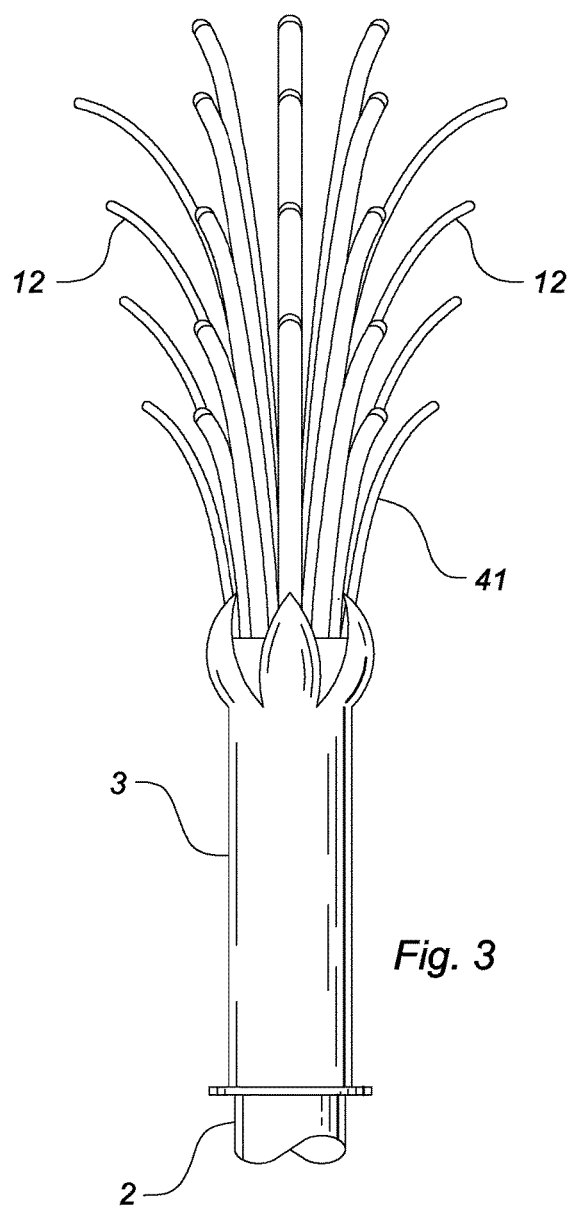
FIG. 3 is a sectional view of the device with the bundled fibers deployed through the frangible leaves.
Figure 4:
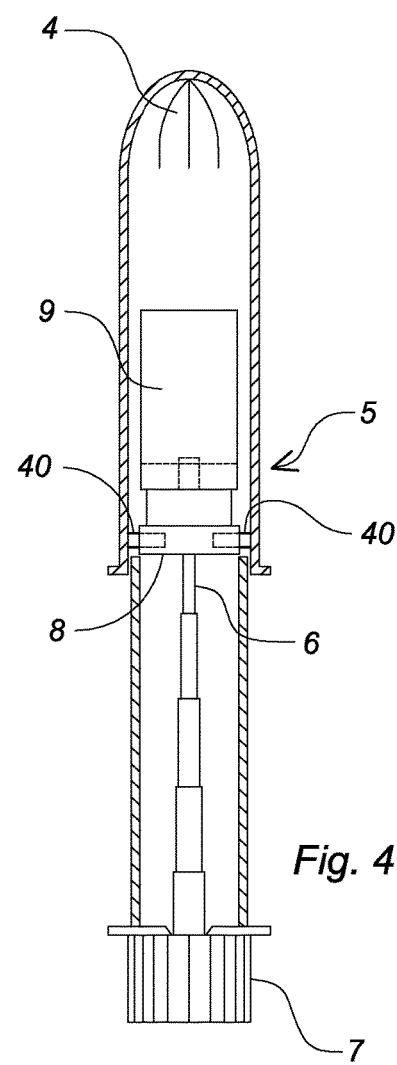
FIG. 4 is a sectional view of the device depicting the internal, deployable absorbing mechanism.
Figure 5:
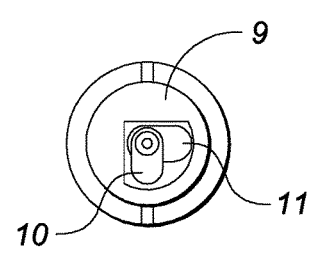
FIG. 5 is an isolated, top view of the cylinder depicting the keyed member offset from the slot to retain the cylinder in an armed position.

The present invention relates to a disposable, feminine-hygiene product comprising an elongated, hollow tube 1 formed of a lower section 2 telescopically received within an upper section 3. The top end 32 of the upper section is formed of a plurality of frangible leaves 4 that immediately separate upon impact. The tube includes a hollow interior having a deployable absorbing mechanism 5 received therein.

The absorbing mechanism includes a telescoping shaft 6 received within the lower section having an upper end and a lower end. The lower end of the shaft is attached to a rotatable knob 7 mounted on a bottom end of the tube. A base plate 8 is attached to the upper end of the shaft and is secured to interior wall of the upper section with a pair of opposing mounting posts 40. The lower section includes a pair of opposing slits in which the mounting posts ride to allow the tube and shaft to be expanded for use as explained below.

Resting on an upper surface of the plate 8 is a spring-biased cylinder 9 that is released to thrust an absorbent member 41 through the frangible leaves. The upper, distal end of shaft includes a keyed member 10 that is initially offset from a mating slot 11 on a lower end of the cylinder to lock the cylinder in an armed position. When the key is rotated into the slot 11, the cylinder is automatically propelled toward the upper end of the tube.

The absorbent member 41 is formed of a plurality of fabric strips 12 that are attached at one end to the bottom interior of the cylinder 9, with a remaining portion compressed within the cylinder and the upper tube section. The strips 12 are constructed with bamboo-fabric fibers, or any other similar material that is both highly absorbent and biodegradable.

Accordingly, to absorb unwanted fluids, a user extends the tube sections to allow the fabric strips to be more easily manipulated within the vaginal cavity. The user inserts the upper section into the vagina and rotates the knob until the keyed member seats within the mating slot to release the cylinder. The spring thrusts the cylinder upwardly, forcing the strips through the frangible leaves to form an absorbent brush head that can be manipulated as necessary to absorb any unwanted fluids. When the user finishes, the entire biodegradable device may be safely discarded.

The above-described device is not limited to the exact details of construction and enumeration of parts provided herein. For example, though the cylinder has been primarily depicted and described as being automatically lifted with a spring, any manual or automatic mechanism may be used to move the cylinder toward the upper end of the tube. Furthermore, the size, shape and materials of construction of the various components can be varied without departing from the spirit of the present invention.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A disposable feminine-hygiene product comprising: an elongated, hollow tube having a top end, a bottom end and a hollow interior, the top end of said tube formed of a plurality of frangible leaves that immediately separate upon impact; a deployable absorbing member received with the interior chamber, said absorbing member formed of a plurality of fabric strips; means for propelling said absorbing member through the frangible leaves to absorb unwanted vaginal fluids, wherein said means for propelling said absorbing member through the frangible leaves comprises: a shaft having an upper end and a lower end with a keyed member at the upper end; a base plate proximal the upper end of the shaft; a spring-biased cylinder resting on said base plate and attached to said absorbing member, said cylinder having a slot thereon that mates with said keyed member so that when said keyed member is rotated into said slot, said cylinder is propelled toward the top end of said tube to thrust said absorbing member through said frangible leaves.

2. The disposable feminine-hygiene product according to claim 1 wherein said plurality of fabric strips are attached to said spring-biased cylinder and compressed within the hollow interior of said tube.

3. The disposable feminine-hygiene product according to claim 2 wherein said strips are constructed with bamboo-fabric fibers.

4. The disposable feminine-hygiene product according to claim 1 wherein the lower end of said shaft is attached to a rotatable knob on the lower tube section to facilitate rotating said keyed member into said slot.

5. The disposable feminine-hygiene product according to claim 1 wherein said tube is formed of a lower section telescopically received within an upper section so that said tube can be extended to facilitate manipulation of said absorbing member.

6. The disposable feminine-hygiene product according to claim 5 wherein said shaft is telescopic to be extensible with said tube.

\* \* \* \* \*